US012564309B2

(12) United States Patent
Dhanotiya et al.

(10) Patent No.: US 12,564,309 B2
(45) Date of Patent: Mar. 3, 2026

(54) ACTUATORS FOR MEDICAL DEVICES AND RELATED SYSTEMS AND METHODS

(71) Applicants: Boston Scientific Medical Device Limited, Galway (IE); Boston Scientific Scimed, Inc., Maple Grove, MN (US)

(72) Inventors: Aditya Dhanotiya, Madhya Pradesh (IN); Balaji Aswatha Narayana, Karnataka (IN); Nabarun Bhowmick, West Bengal (IN); Shrikant Vasant Raut, Maharashtra (IN); James Weldon, Newton, MA (US)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 405 days.

(21) Appl. No.: 18/165,559

(22) Filed: Feb. 7, 2023

(65) Prior Publication Data

US 2023/0248213 A1     Aug. 10, 2023

Related U.S. Application Data

(60) Provisional application No. 63/307,762, filed on Feb. 8, 2022.

(51) Int. Cl.
*A61B 1/00* (2006.01)
*A61B 1/045* (2006.01)

(52) U.S. Cl.
CPC ...... *A61B 1/00068* (2013.01); *A61B 1/00042* (2022.02); *A61B 1/045* (2013.01)

(58) Field of Classification Search
CPC ............ A61B 1/00042; A61B 1/00066; A61B 1/00068; A61B 1/045; A61B 1/052
See application file for complete search history.

(56) References Cited

U.S. PATENT DOCUMENTS 4,198,958 A * 4/1980 Utsugi ............... A61B 1/00137
                                                      600/154
4,760,838 A * 8/1988 Fukuda .............. A61B 1/00068
                                                      600/158
(Continued)

FOREIGN PATENT DOCUMENTS

EP       2502548 A1    9/2012
EP       3592199 B1    6/2021
(Continued)

OTHER PUBLICATIONS

International Search Report and Written Opinion issued in International Application No. PCT/US2023/062116, issued May 11, 2023 (10 pages).

*Primary Examiner* — Aaron B Fairchild
(74) *Attorney, Agent, or Firm* — Bookoff McAndrews PLLC

(57) ABSTRACT

According to one aspect, a handle assembly for a medical device may comprise a handle body; and an actuator for controlling a supply of air and a supply of liquid to the medical device. The actuator may comprise a button including a hole extending through a top surface of the button, and the hole may be offset from a center of the top surface of the button. The actuator may be configured to: supply air to the medical device when a user covers the hole; and/or supply liquid to the medical device when a user presses the button.

14 Claims, 3 Drawing Sheets

(56)                    References Cited

U.S. PATENT DOCUMENTS

| 5,007,406 | A | 4/1991 | Takahashi et al. |
| 5,228,646 | A * | 7/1993 | Raines ............... A61B 1/00068 |
| | | | 251/324 |
| 5,601,601 | A | 2/1997 | Tal et al. |
| 6,346,075 | B1 * | 2/2002 | Arai ................... A61B 1/00068 |
| | | | 600/159 |
| 6,520,908 | B1 | 2/2003 | Ikeda et al. |
| 7,008,355 | B2 | 3/2006 | Emick |
| 8,092,373 | B1 | 1/2012 | Papouras et al. |
| 2013/0190566 | A1 | 7/2013 | Miyoshi et al. |
| 2014/0081266 | A1 | 3/2014 | DuBois et al. |
| 2014/0243594 | A1 | 8/2014 | Raybin et al. |
| 2016/0135872 | A1 | 5/2016 | Minnelli et al. |
| 2019/0208988 | A1 | 7/2019 | Takatsuji et al. |
| 2020/0187756 | A1 | 6/2020 | Maurice |
| 2020/0323418 | A1 | 10/2020 | Narayana et al. |
| 2020/0355281 | A1 * | 11/2020 | Harris ................ A61B 1/00137 |
| 2021/0137361 | A1 | 5/2021 | Kubo |

FOREIGN PATENT DOCUMENTS

| JP | S63214228 | A | 9/1988 |
| JP | 2000287917 | A | 10/2000 |
| JP | 2005230183 | A | 9/2005 |
| JP | 2006149877 | A | 6/2006 |
| JP | 2006149880 | A | 6/2006 |
| JP | 2006212048 | A | 8/2006 |
| JP | 4856109 | B2 | 1/2012 |
| JP | 5448637 | B2 | 3/2014 |
| JP | 5985468 | B2 | 9/2016 |
| JP | 3233608 | U | 8/2021 |
| KR | 101764526 | B1 | 8/2017 |

* cited by examiner

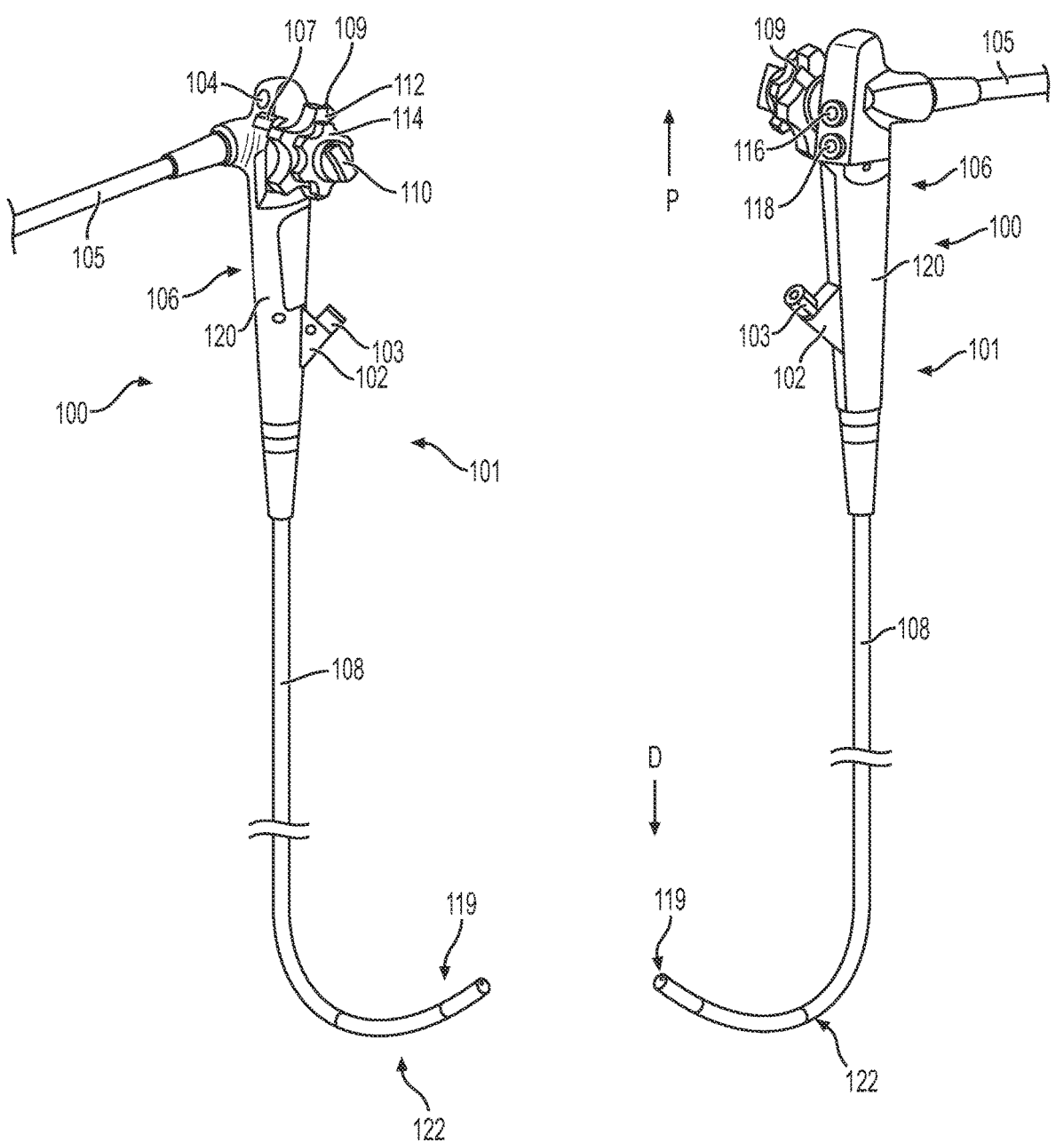
FIG. 1A          FIG. 1B

ACTUATORS FOR MEDICAL DEVICES AND RELATED SYSTEMS AND METHODS

CROSS-REFERENCE TO RELATED APPLICATION(S)

This application claims the benefit of priority of U.S. Provisional Application No. 63/307,762, filed Feb. 8, 2022, the entirety of which is incorporated by reference herein

TECHNICAL FIELD

Various aspects of this disclosure relate generally to actuators for handles of medical devices. More specifically, embodiments of this disclosure relate to ergonomic actuators for use with a handle of an endoscope or other medical device, among other aspects.

BACKGROUND

During endoscopic procedures, the medical professional operating the endoscope often wraps his/her entire palm around a grip or handle portion of the device. Various actuators on the handle of the endoscope require the medical professional to contort his/her hands frequently and for prolonged periods of time during a procedure, which can cause strain, or even an injury. In some cases, actuation of different scope controls, like knobs or an elevator actuator, may result in excessive movements of the medical professional's thumb or other fingers, which may result in strain in the medical professional's hand. Endoscope operators can experience wrist and hand discomfort resulting from holding and manipulating the endoscope's handle. In some cases, medical professionals may experience symptoms similar to those of Carpal Tunnel Syndrome or tendonitis. When a medical professional experiences fatigue or other pain in the fingers, hand, or wrist, the medical professional may shift from a primary grip position to a secondary grip position that may be a less powerful grip than the primary grip position, such as shifting from a four finger grip to a three finger grip. Repeatedly reaching or contorting the fingers to access various actuators can increase fatigue or other pain.

When a medical professional repeatedly readjusts his or her hand grip in between procedure tasks, the procedure may be prolonged and procedural tasks may be more difficult. Depending on the size of a medical professional's hand, actuators may be positioned in non-optimized positions and increase the number of readjustments of the professional's hand during a procedure.

SUMMARY

Aspects of the disclosure relate to, among other things, systems, devices, and methods for assisting a user's access to actuators on a handle and facilitate a user's hand grip on an endoscope or other medical device. Endoscopes and other medical devices with actuators configured to accommodate various sizes of fingers and hands may help address user hand fatigue or strain, may help reduce the need for hand grip readjustments, and may help address other issues. Each of the aspects disclosed herein may include one or more of the features described in connection with any of the other disclosed aspects.

According to one aspect, a handle assembly for a medical device may comprise a handle body; and an actuator for controlling a supply of air and a supply of liquid to the medical device. The actuator may comprise a button including a hole extending through a top surface of the button, and the hole may be offset from a center of the top surface of the button. The actuator may be configured to: supply air to the medical device when a user covers the hole; and/or supply liquid to the medical device when a user presses the button.

In other aspects, the handle assembly may include one or more of the following features. The button may be received by a base portion of the handle body. The handle assembly may further include a knob actuator, and the hole may be positioned between the center of the button and the knob actuator. The button may be oval shaped and the handle body may include a distal portion and a proximal portion, the proximal portion including a protruding portion protruding radially outwardly from a central longitudinal axis of the handle body such that a cross-sectional size of the proximal portion is greater than a cross-sectional size of the distal portion; and the base portion may be positioned entirely on the protruding portion. The top surface of the button may face away from a side of the handle body, and a top surface of an image capture button may face away from the side of the handle body, the image capture button configured to control an image sensor of the medical device. The actuator may be a first actuator and the button may be a first button, and the handle assembly may further comprise a second actuator for controlling a supply of suction to the medical device, the second actuator including a second button positioned entirely on the protruding portion adjacent to the first actuator. The protruding portion may be a first protruding portion, the image capture actuator may be positioned at a second protruding portion of the handle body, and the second protruding portion may protrude outwardly in a direction transverse to the first protruding portion.

In other aspects, the handle assembly may include one or more of the following features. The button may be rectangular shaped and may extend longitudinally from a first end towards a knob actuator of the handle assembly, defining an empty gap between the button and the knob actuator. The actuator may be a first actuator, the button may be a first button, and the empty gap may be a first empty gap, wherein the handle assembly further comprises a second actuator for controlling a supply of suction to the medical device, wherein the second actuator is positioned adjacent to the first actuator, and includes a second button, wherein the second button is rectangular shaped and extends longitudinally from a second end towards the knob actuator of the handle assembly, defining a second empty gap between second button and the knob actuator. The button may include a first surface and a second surface, and the first surface may be a radially-outermost surface relative to a central longitudinal axis of the handle body and is substantially planar, and the second surface may be a radially-outermost surface, relative to the central longitudinal axis, and extends radially outwardly from a first end to the first surface. The second surface may be a curved, concave surface. The hole may be in the second surface. The handle assembly may further comprise a knob actuator, and the first surface may be positioned closer to the knob actuator than the second surface. The actuator may be a first actuator and the button may be a first button, and the handle assembly may further comprise a second actuator for controlling a supply of suction to the medical device. The second actuator may be positioned adjacent to the first actuator and may include a third surface and a fourth surface; the third surface may be a radially-outermost surface relative to a central longitudinal axis of the handle body and may be substantially planar; and the fourth surface may be a radially-outermost surface, relative to the central longitudinal axis, and may extend radially outwardly from a second end to the third surface. A first distance from the first surface of the button to a radially-outer edge of the handle body, relative to a central longitudinal axis of the handle body, directly opposite the button may be approximately 70 millimeters, and a second distance from a radially-outermost portion of the first end to the radially-outer edge of the handle body, relative to a central longitudinal axis of the handle body, directly opposite the button may be approximately 60 millimeters.

In another aspect, a handle assembly for a medical device may comprise a handle body; and an actuator for controlling one or more functions of the medical device. The actuator may comprise a button including a first surface and a second surface, and the first surface may be a radially-outermost surface relative to a central longitudinal axis of the handle body and may be substantially planar. The second surface may be a radially-outermost surface, relative to the central longitudinal axis, may extend radially outwardly from a first end to the first surface, and may be concave.

In other aspects, the handle assembly may include one or more of the following features. The actuator may be configured to: (i) supply air to the medical device when a user covers a hole of the button, and supply liquid to the medical device when a user presses the button; or (ii) supply suction to the medical device when a user presses the button. The button may include a hole in a top surface of the button, and the hole may be spaced from a center of the button. A first distance from the first surface of the button to a radially-outer edge of the handle body, relative to a central longitudinal axis of the handle body, directly opposite the button may be approximately 70 millimeters, and a second distance from a radially-outermost portion of the first end to the radially-outer edge of the handle body, relative to a central longitudinal axis of the handle body, directly opposite the button may be approximately 60 millimeters.

In other aspects, a method of operating an endoscope that includes a handle may include (i) gripping the handle to hold the endoscope; (ii) covering a hole of a first button to supply air to a distal end of the endoscope; and (iii) displaying on an electronic display a total amount of air supplied to the distal end of the endoscope.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of this disclosure and together with the description, serve to explain the principles of the disclosure.

FIGS. 1A and 1B are perspective views of an exemplary endoscope, according to aspects of this disclosure.

DETAILED DESCRIPTION

Figures 2A, 2B:
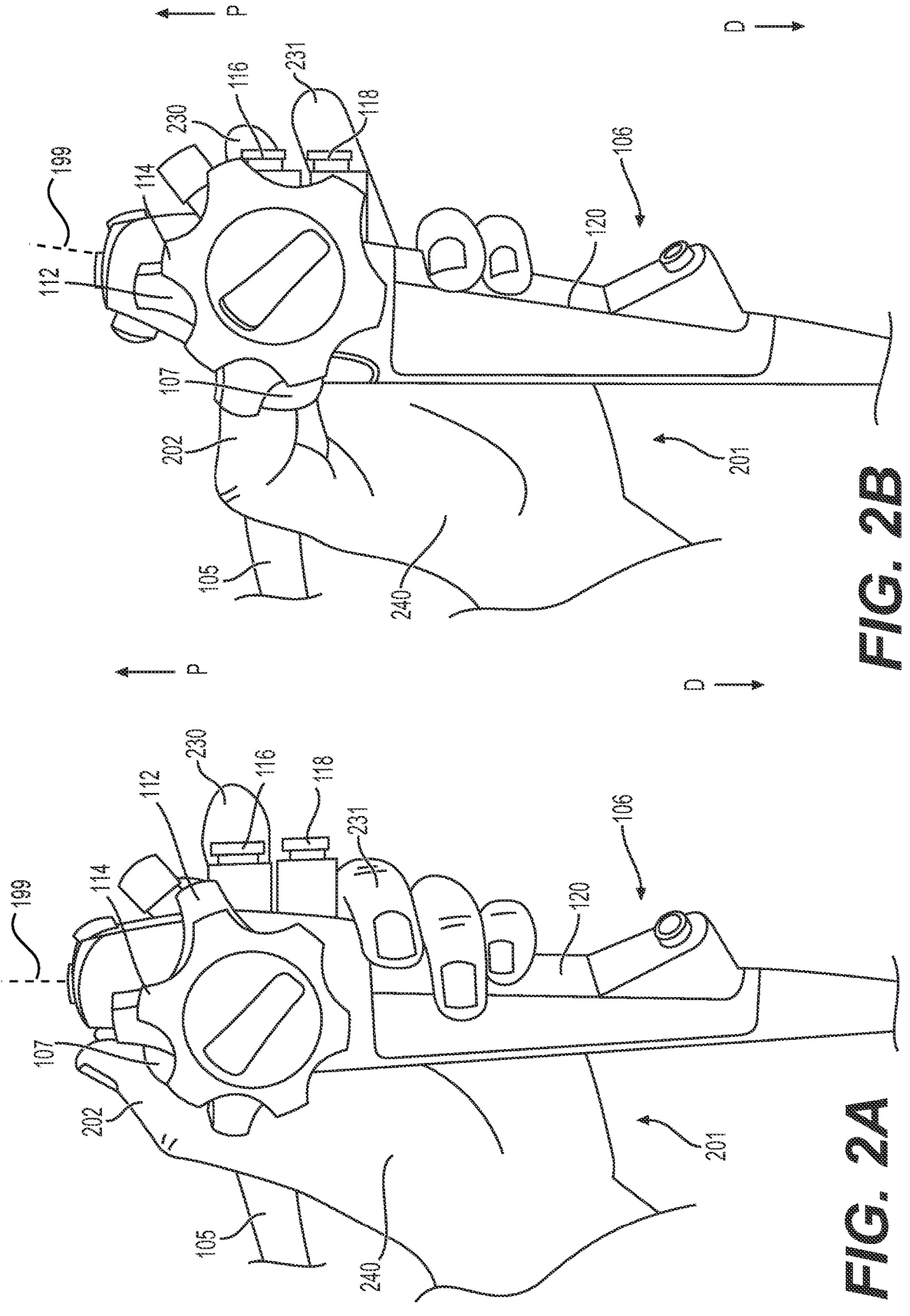
FIGS. 2A and 2B are perspective views of a user's hand holding an endoscope handle, according to aspects of this disclosure.

Reference will now be made in detail to aspects of this disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. Throughout the figures included in this application, arrows labeled "P" and "D" are used to show the proximal and distal directions in the figure. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Further, relative terms such as, for example, "about," "substantially," "approximately," etc., are used to indicate a possible variation of ±10% in a stated numeric value or range.

Embodiments of this disclosure seek to improve a user's ability to grip, manipulate, and otherwise apply force to a handle, and actuators of the handle, of a medical device, such as an endoscope, during a medical procedure and, as non-limiting exemplary benefits, help reduce the need to reposition a user's hand during a procedure and reduce strain to a user's hand from excessive movement of fingers, among other aspects. In addition, aspects of this disclosure may facilitate accommodating an ergonomic grip on a handle for a plurality of different hand sizes.

FIGS. 1A and 1B show a perspective view of an exemplary endoscope system 100. Endoscope system 100 may include an endoscope 101. Endoscope 101 may include a handle assembly 106 and a flexible tubular shaft 108. The handle assembly 106 may include a biopsy port 102, a biopsy cap 103, an image capture button 104, an elevator actuator 107, a first locking lever 109, a second locking lever 110, a first control knob 112, a second control knob 114, a suction button 116, an air/water button 118, a handle body 120, and an umbilicus 105. All of the actuators, elevators, knobs, buttons, levers, ports, or caps of endoscope system 100 may serve any purpose and are not limited by any particular use that may be implied by the respective naming of each component used herein. The umbilicus 105 may extend from handle body 120 to auxiliary devices, such as a control unit, water supply, and/or vacuum source. Umbilicus 105 therefore can transmit signals between endoscope 101 and the control unit, to control lighting and imaging components of endoscope 101 and/or receive image data from endoscope 101. Umbilicus 105 also can provide fluid for air for insufflation, irrigation from the water supply, and/or suction to a distal tip 119 of shaft 108. Buttons 116 and 118 control valves for suction and fluid (air/water) supply, respectively. Shaft 108 may terminate at a distal tip 119. Shaft 108 may include an articulation section 122 for deflecting distal tip 119 in up, down, left, and/or right directions. Knobs 112 and 114 may be used for controlling such deflection, and locking levers 109 and 110 may lock knobs 112 and 114, respectively, in desired positions. Handle body 120 may be tapered and may narrow as the handle extends distally such that the profile of the handle body 120 is smaller at its distal end than at its proximal end.

Distal tip 119 may include an imaging device (e.g., a camera) and a lighting source (e.g., an LED or an optical fiber). Distal tip 119 may be side-facing. That is, imaging device and lighting source may face radially outward, perpendicularly, approximately perpendicularly, or otherwise transverse to a longitudinal axis of shaft 108 and distal tip 119.

Although the term endoscope may be used herein, it will be appreciated that other devices, including, but not limited to, duodenoscopes, colonoscopes, ureteroscopes, bronchoscopes, laparoscopes, sheaths, catheters, or any other suitable delivery device or medical device may be used in connection with the devices of this disclosure, and any of the actuator embodiments discussed herein may be incorporated into any of these or other medical devices.

In operating endoscope system 100, a user may use his/her left hand to hold the handle assembly 106 (shown in FIG. 2A) while the right hand is used to hold accessory devices and/or operate one or more of the actuators of the handle assembly 106, such as the first and second control knobs 112, 114 and the first and second locking levers 109, 110. The user may grasp the handle assembly 106 by wrapping the user's hand around the handle body 120. When grasping handle body 120, the user may use the left thumb to operate the first and second control knobs 112, 114 and the elevator actuator 107 (through rotation about their axis), and may use a left-hand finger to operate the image capture button 104, the suction button 116, and the air/water button 118 (each by pressing).

FIGS. 2A and 2B show an exemplary user's left hand 201 grasping handle assembly 106. The user's left index finger 230 and middle finger 231 may be used to operate the suction button 116 and the air/water button 118. A user may have to reach and/or strain his/her index or middle finger to actuate the suction button 116 and/or the air water button 118. The actuators discussed herein below may help reduce the reach required and/or alleviate strain to a user's fingers and/or hand. Handle assembly 106 may have a central longitudinal axis 199 extending longitudinally through handle assembly 106.

The user may position the thumb 202 of the grasping hand 201 over the elevator actuator 107 and move the elevator actuator 107 along a circular path from a first position (shown in FIG. 2A) to a second position (shown in FIG. 2B) by moving the thumb 202. As shown in FIG. 2B, the palm 240 may move away from the handle body 120 when the thumb 202 moves from the first position to the second position, and a user may have difficulty reaching the suction button 116 and/or the air water button 118 with the index or middle fingers when the palm 240 moves away from the handle body 120. The actuators discussed herein below may help reduce the movement required of the index and/or ring fingers to actuate the suction button 116 and/or the air water button 118 during operation of endoscope 101.

Figures 3A, 3B, 3C, 4, 5, 6A, 6B:
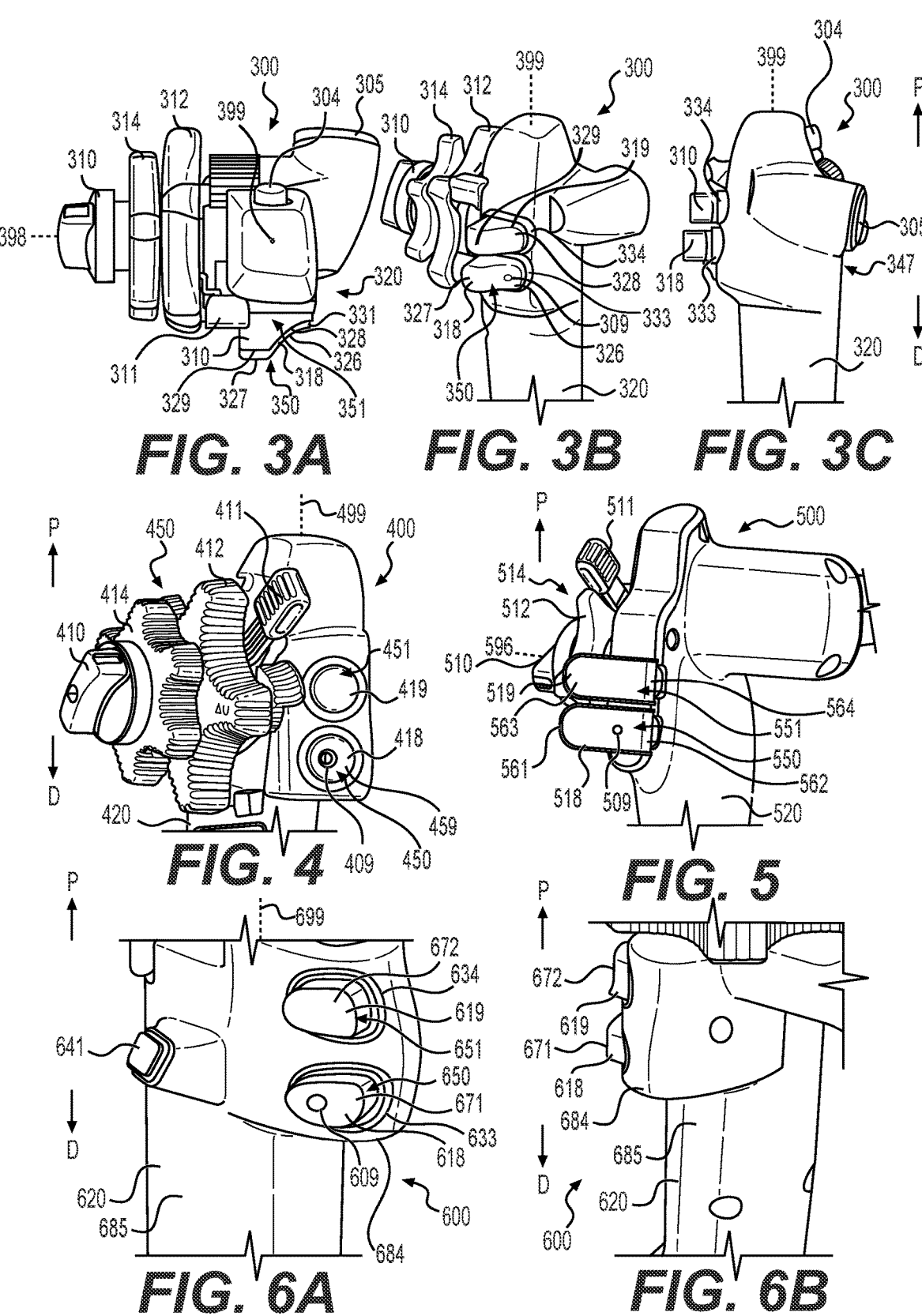
FIGS. 3A, 3B and 3C are top, perspective, and side views, respectively, of a proximal portion of an endoscope handle, according to aspects of this disclosure.
FIG. 4 is a perspective view of a proximal portion of an endoscope handle, according to aspects of this disclosure.
FIG. 5 is a perspective view of a proximal portion of an endoscope handle, according to aspects of this disclosure.
FIGS. 6A and 6B are perspective and side views, respectively, of a proximal portion of an endoscope handle, according to aspects of this disclosure.

FIGS. 3A, 3B, and 3C show a top view, a perspective view, and a side view of an alternative handle assembly 300 including an image capture button 304, a first locking lever 311, a second locking lever 310, a first control knob 312, a second control knob 314, an air/water actuator 350 including air/water button 318, a suction actuator 351 including suction button 319, a handle body 320, and an umbilicus/umbilicus connector 305. A central rotational knob axis 398 may extend through first control knob 312 and second control knob 314.

Air/water button 318 may be configured to control supply of air and liquid/water to a distal portion of the medical device. Air/water button 318 may include a first surface 326 that is curved and extends from a first end 331 to a second surface 327. First surface 326 may be a concave surface and may extend radially-outward, relative to central longitudinal axis 399, from the first end 331, and second surface 327 may be substantially planar and may be the radially-outermost portion, relative to central longitudinal axis 399, of air/water button 318. Central longitudinal axis 399 is shown extending through the page in FIG. 3A. Second surface 327 may be positioned closer to first control knob 312 and second control knob 314 than first surface 326. The width of handle body 320 from a radially-outermost portion of air/water button 318, relative to axis 399, to an opposite side 347 of handle body 320 may increase as air/water button 318 extends towards first control knob 312.

In some examples, the width of handle body 320 from a radially-outermost portion of air/water button 318, relative to axis 399, to an opposite side 347 of handle body 320, such as a radially-outer edge of the handle body on the opposite side 347, may increase from approximately 60 mm to approximately 70 mm (inclusive) as air/water button 318 extends towards first control knob 312. Air/water button 318 may include a lumen leading to a hole 309 configured to allow airflow from an air source to vent out of handle body 320. Hole 309 may be positioned on first surface 326, and hole 309 may be spaced from the center of air/water button 318. In other examples, air/water button 318 may include tiered surfaces with each of first surface 326 and second surface 327 being substantially planar and first surface 326 not having any curvature (not shown). By having first surface 326 curved and/or tiered relative to second surface 327, air/water button 318 may accommodate several different hand sizes by allowing access to air/water button 318 at a plurality of circumferences of handle body 320. Depending on a user's hand and/or finger size, the user may access air/water button 318 at first surface 326, second surface 327, or both first surface 326 and second surface 327. For example, a user may wrap his/her fingers around a smaller portion of the circumference of the handle body 320 to access first surface 326 of air/water button 318 when gripping handle body 320, compared to if the user wraps his/her fingers around a larger portion of the circumference of the handle body 320 to access second surface 327 of air/water button 318 when gripping handle body 320.

Suction button 319 may include a first surface 328 and a second surface 329. First surface 328 and second surface 329 may have any of the attributes discussed regarding first surface 326 and second surface 327. First surface 328 may be longitudinally aligned with first surface 326, and second surface 329 may be longitudinal aligned with second surface 327. In some examples, first surface 328 may be spaced from central longitudinal axis 399 the same distance as first surface 326 is spaced from central longitudinal axis 399, and second surface 329 may be spaced from central longitudinal axis 399 the same distance as second surface 327 is spaced from central longitudinal axis 399.

Handle body 320 may include a first base portion 333 configured to receive air/water button 318 and a second base portion 334 configured to receive suction button 319. In some examples, first base portion 333 and second base portion 334 are molded as part of and integral with handle body 320. First base portion 333 and second base portion 334 may be substantially rectangular or ovular, may extend circumferentially about central axis longitudinal axis 399, and may be positioned adjacent to first control knob 312 and on an opposite side, relative to axis 399, as image capture button 304. Air/water button 318 may be configured to move within first base portion 333 and towards central longitudinal axis 399 when a user presses on air/water button 318, and suction button 319 may be configured to move within second base portion 334 and towards central longitudinal axis 399 when a user presses on suction button 319.

FIG. 4 shows a perspective view of a proximal portion of an alternative handle assembly 400. Handle assembly 400 may include a first locking lever 411, a second locking lever 410, a first control knob 412, a second control knob 414, an air/water actuator 450 including air/water button 418, a suction actuator 451 including suction button 419, and a handle body 420. Air/water button 418 may be circular in cross-section and may include a lumen leading to a hole 409 in a radially-outer top surface 459 of button 418. The lumen and hole 409 are configured to allow airflow from an air source to vent out of handle body 420. Hole 409 may be offset and/or spaced from a center of surface 459 of air/water button 418. In some examples, hole 409 may be positioned in a first half surface 459 of air/water button 418 closer to first control knob 412, which may help prevent accidental insufflation or application of an air supply to a distal portion of the medical device and may prevent accidental covering of hole 409 by a user's finger. By positioning hole 409 off-center, closer to control knob 412, sufficient surface area of surface 459 remains for a user to place a finger on surface 459 without covering hole 409. In some examples, top surface 459 of air/water button 418 may be inclined or declined in a direction of a circumference about central longitudinal axis 499 of handle body 420, toward or away from knobs 412/414.

FIG. 5 shows a perspective view of a proximal portion of an alternative handle assembly 500. Handle assembly 500 may include a first locking lever 511, a second locking lever 510, a first control knob 512, a second control knob 514, an air/water actuator 550 including air/water button 518, a suction actuator 551 including suction button 519, and a handle body 520. Air/water button 518 may be substantially rectangular (with rounded corners) or ovular in shape and may extend from a first end 561 adjacent to first control knob 512 to a second end 562 adjacent to handle body 520. Air/water button 518 may include a lumen leading to a hole 509 in a radially-outer top surface of button 518 and configured to allow airflow from an air source to vent out of handle body 520. Hole 509 may be offset and/or spaced from a center of the radially-outer top surface of air/water button 518, and may be positioned at any location on the at surface. The radially-outer top surface of each of air/water button 518 and suction button 519 may be planar and extend longitudinally parallel to central knob axis 596. The radially-outer top surface of suction button 519 may be substantially rectangular (with rounded corners) or ovular in shape and may extend from a first end 563 adjacent from first control knob 512 to a second end 564 adjacent from handle body 520. Air/water button 518 and suction button 519 may have sufficient longitudinal length such that first end 561 and first end 563 each may overhang first control knob 512, and may create a first gap between first control knob 512 and air/water button 518, and a second gap between suction button 519 and first control knob 512. A portion of air/water button 518 may extend away from handle body 520 in the direction of knob axis 596, and a portion of suction button 519 may extend away from handle body 520 in the direction of knob axis 596.

FIGS. 6A and 6B show perspective views of a proximal portion of an alternative handle assembly 600. Handle assembly 600 may include an air/water actuator 650 including air/water button 618, a suction actuator 651 including suction button 619, a handle body 620, and an image capture button 641. Handle assembly 600 may have any of the features discussed herein in relation to the other handle assemblies 106, 300, 400, 500. Air/water button 618 may be oval shaped in cross-section, and may include a concave top surface 671 and a lumen leading to a hole 609 in top surface 671 and configured to allow airflow from an air source to vent out of handle body 620. Hole 609 may be offset from a center of top surface 671, as in embodiments described above. Suction button 619 may include a concave top surface 672 and may be positioned adjacent to air/water button 618. Each of air/water button 618 and suction button 619 may be received by base portions 633, 634, respectively, on handle body 620. Handle body 620 may include a distal portion 685 and a protruding portion 684 at a proximal portion of handle body 620. Protruding portion 684 may protrude radially outward, relative to a central longitudinal axis 699 of handle body 620, from distal portion 685 of handle body 620. Each of air/water button 618 and suction button 619 may be positioned entirely on protruding portion 684, and each of base portions 633, 634 may be integral with and part of protruding portion 685. The circumference of handle body 620 about axis 699, including protruding portion 684, may be larger than the circumference, about axis 699, of handle body 620 at distal portion 685. Each of the top surfaces 671, 672 of air/water button 618 and suction button 619 may extend longitudinally at an angle relative to central axis 699 and a central knob axis of handle assembly 600, inclined toward image capture button 641 and a user of the device and inclined.

Image capture button 641 may protrude radially outward from handle body 620 and may extend towards and face the proximal direction as image capture button extends radially outward. Image capture button 641 may be spaced from protruding portion 685 and may be rectangular in shape. The radially-outer top surface of image capture button 641 faces the same side of handle body 620 as the side of handle body 620 that surfaces 671, 672 of buttons 618, 619 face.

In general, air water actuators 318, 418, 518, 618 allow a user to supply a flow of pressurized air to a patient's anatomy through one or more channels of an endoscope or other medical device. When a user leaves hole 309, 409, 509, 609 of air/water button 318, 418, 518, 618 un-covered, air flow from an air supply is allowed to vent to the atmosphere outside of the medical device and the patient. When a user covers hole 309, 409, 509, 609 of air/water button 318, 418, 518, 618 with a finger or other part of the user's body, air flow from the air supply flows through the endoscope or other medical device and exits out of a distal end of the device into the patient's anatomy. To supply water to the distal end of the endoscope or other device, a user has to press air/water button 318, 418, 518, 618 to supply liquid, such as water, to a water channel of the endoscope or other device. When a user releases air/water button 318, 418, 518, 618, the supply of liquid to the distal end of the endoscope or other device stops.

In some aspects of this disclosure, a flow meter and/or flow sensor may be incorporated into a handle assembly 106, 300, 400, 500, 600 to monitor the airflow and/or quantity of air supplied to the patient. The status of the amount of air injected may be electronically displayed by an electronic display connected, wirelessly or via one or more wires, to the handle assembly 106, 300, 400, 500, 600. The status of the amount of air injected to the patient may be displayed via a graphical user interface and/or auditory feedback may be provided to the user, such as alert messages of the total quantity of air injected into the patient. In some examples, a bar graph on a graphical user interface may depict the total amount of air injected, and the bar graph may change colors (such as from blue to red) when a threshold level of air has been reached, for example signifying that a potentially dangerous total amount of air has been supplied to the patient. In some examples, a pressure transducer may be positioned at a distal portion of the device and may be used to measure a threshold amount of pressure due to the air injected into the patient. In some examples, a compressible gas reading device may be used to monitor air injected.

Handle assembly 106, 300, 400, 500, 600 and buttons/ actuators 318, 319, 418, 419, 518, 519, 618, 619 of this disclosure may assist with ergonomically positioning fingers of the user when the user operates endoscope 101 or other medical devices, may reduce hand strain caused by excessive movement and/or reaching of fingers when the user operates endoscope 101, and may reduce the chance of the user losing his or her grip. Also, the handle assemblies 106, 300, 400, 500, 600 and actuators 318, 319, 418, 419, 518, 519, 618, 619 may help prevent repeated repositioning of a user's hand on a medical device handle due to fatigue, strain, or other difficulty. Each of the aforementioned handle assemblies 106, 300, 400, 500, 600 and actuators 318, 319, 418, 419, 518, 519, 618, 619, whether used in conjunction with an endoscope system or any other medical device, may be used to enhance and/or facilitate a user's grip on a handle. Any portion of the handle assemblies or actuators discussed herein may be incorporated into a handle of an endoscope or other medical device to improve a user's operation of the device. Handle assemblies 106, 300, 400, 500, 600 and actuators 318, 319, 418, 419, 518, 519, 618, 619 of this disclosure may allow multiple users with different size hands and/or fingers to comfortably use the same handle assembly.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and embodiments be considered as exemplary only.

We claim:

1. A handle assembly for a medical device comprising:
a handle body; and
an actuator for controlling a supply of air and a supply of liquid to the medical device, the actuator comprising:
a button including a hole extending through a top surface of the button, wherein a center of the hole is offset from a center of the top surface of the button;
wherein the actuator is configured to:
supply air to the medical device when a user covers the hole; and/or
supply liquid to the medical device when a user presses the button.

2. The handle assembly of claim 1, wherein the button is received by a base portion of the handle body.

3. The handle assembly of claim 1, further comprising a knob actuator, and wherein the center of the top surface of the button is positioned between the hole and the knob actuator.

4. The handle assembly of claim 1, wherein the button includes a first surface and a second surface, wherein the first surface is a radially-outermost surface relative to a central longitudinal axis of the handle body and is substantially planar, and wherein the second surface is a radially-outermost surface, relative to the central longitudinal axis, and extends radially outwardly from a first end to the first surface.

5. The handle assembly of claim 4, wherein the second surface is a curved, concave surface.

6. The handle assembly of claim 4, wherein the hole is in the second surface.

7. The handle assembly of claim 4, further comprising a knob actuator, and wherein a distance from the first surface to the knob actuator is less than a distance from the second surface to the knob actuator.

8. The handle assembly of claim 4,
wherein the actuator is a first actuator and the button is a first button,
wherein the handle assembly further comprises a second actuator for controlling a supply of suction to the medical device,
wherein the second actuator is positioned adjacent to the first actuator and includes a third surface and a fourth surface,
wherein the third surface is a radially-outermost surface relative to a central longitudinal axis of the handle body and is substantially planar, and
wherein the fourth surface is a radially-outermost surface, relative to the central longitudinal axis, and extends radially outwardly from a second end to the third surface.

9. The handle assembly of claim 4, wherein a first distance from the first surface of the button to a radially-outer edge of the handle body, relative to a central longitudinal axis of the handle body, directly opposite the button is approximately 70 millimeters, and wherein a second distance from a radially-outermost portion of the first end to the radially-outer edge of the handle body, relative to a central longitudinal axis of the handle body, directly opposite the button is approximately 60 millimeters.

10. A handle assembly for a medical device comprising:
a handle body having a top, proximal end and a bottom, distal end; and
an actuator for controlling a supply of air and a supply of liquid to the medical device, the actuator comprising:
a button including a hole and extending from the handle body, wherein the button includes:
a first surface transverse to the handle body and facing proximally,
a second surface that is curved,
a third surface that is a radially outermost surface of the button, and
a fourth surface transverse to the handle body and facing distally,
wherein the first surface meets the second and third surfaces at a first edge, the fourth surface meets the second and third surfaces at a second edge, the second surface meets the third surface at a third edge, and
wherein a user of the actuator can press on the second surface towards the handle body to move the button radially inward, and the user can press on the third surface towards the handle body to move the button radially inward
wherein the actuator is configured to:
supply air to the medical device when a user covers the hole; and/or
supply liquid to the medical device when a user presses the button;
wherein the second surface is concave.

11. The handle assembly of claim 10, wherein the third surface is substantially planar.

12. The handle assembly of claim 10, wherein the second and third surfaces together comprise a top surface of the button, and a center of the hole is offset from a center of the top surface.

13. The handle assembly of claim 10, wherein the hole is in the second surface.

14. The handle assembly of claim 10, further comprising a knob actuator, and wherein a distance from the third surface to the knob actuator is less than a distance from the second surface to the knob actuator.

* * * * *